United States Patent
Stokes et al.

[11] Patent Number: 5,851,837
[45] Date of Patent: Dec. 22, 1998

[54] METHOD FOR DETERMINATION OF SALT STOICHIOMETRY

[75] Inventors: Edward Brittain Stokes, Schenectady, N.Y.; Thomas Link Guggenheim, Mt. Vernon; James Marshall Finan, Evansville, both of Ind.

[73] Assignee: General Electric Company, Schenectady, N.Y.

[21] Appl. No.: 795,839

[22] Filed: Feb. 6, 1997

[51] Int. Cl.$^6$ .......................... G01N 27/00; G01N 29/00
[52] U.S. Cl. .............. 436/149; 436/79; 436/85; 436/131; 436/150; 436/183; 568/721; 568/722; 568/723; 568/724
[58] Field of Search ..................... 436/149, 150, 436/18, 32, 79, 85, 131; 568/721, 722, 723, 724

[56] References Cited

U.S. PATENT DOCUMENTS

| | | | |
|---|---|---|---|
| 3,960,968 | 6/1976 | Vernaleken et al. | 568/721 |
| 4,202,993 | 5/1980 | Takekoshi | 568/723 |
| 4,410,735 | 10/1983 | Dellacoletta et al. | |
| 4,492,806 | 1/1985 | Mendiratta et al. | 568/723 |
| 4,546,207 | 10/1985 | Mendiratta et al. | 568/723 |

FOREIGN PATENT DOCUMENTS

| | | |
|---|---|---|
| 63-27448 | 2/1988 | Japan . |
| 2-59536 | 2/1990 | Japan . |

OTHER PUBLICATIONS

M. A. Averbukh et al, *Tr. Vses. Nauch.–Iss/ed. Konstr. Inst. "Tsvetmetautomatika"* 1971 , 74–83.
Averbulch et al., *Chem. Abstr.* 1973, 79, 61141.
J. Balej et al. *Collect. Czech. Chem. Commun.* 1974, 39, 49–56.
S.V. Nemilou et al. *Fiz. Khim. Stekla* 1977, 3, 92–94.
I. P. Storozhuk et al, *Vysokomol. Soedin., Ser A*, 1977, 14, 1800–1806.
V. G. Shapovalov et al. *Tsvetn. Met*, 1978, 83–85.
S. Koda et al, *Biophys. Chem.* 1987, 28, 115–120.
T. L. Guggenheim et al. *Polym. Prepr,* 1989, 30, 579–580.
P. I. Stal'nov *J. Anal. Chem. USSR* 1989, 44, 827–833.
P. I Stal'nov *J. Anal. Chem. USSR.* 1990, 45, 625–633.
A. Bhatnagar et al. *Macromol. Chem. Phys.* 1996, 197, 315–328.

*Primary Examiner*—Arlen Soderquist
*Attorney, Agent, or Firm*—Ernest G. Cusick; Noreen C. Johnson

[57] ABSTRACT

A method for making bisphenol salt as the result of the reaction between bisphenol and an alkali metal hydroxide. The method comprising steps to obtain the anhydrous alkali metal bisphenoxide salt within about a 0.2 mol % stoichiometry relationship between bisphenol and alkali metal hydroxide. A method for determining stoichiometry error of a sample comprises determining variables and applying the variables to an equation to determine stoichiometry.

17 Claims, 5 Drawing Sheets

METHOD FOR DETERMINATION OF SALT STOICHIOMETRY

BACKGROUND OF THE INVENTION

1. Field of the Invention

The invention is directed to a method for a determination of stoichiometry. In particular, the invention is directed to a method of BPA (bisphenol A, isopropylidenediphenol) disodium salt production and stoichiometry determination that allows a real time measurement of stoichiometry, with minimal sampling, extraction, and chromatography steps.

2. Description of Related Art

The stoichiometry or ratio of bisphenol A (BPA) to a caustic sodium hydroxide is a key feature in preparing dry BPA disodium salt. Dry BPA disodium salt is used for a displacement reaction in which bisimide (BI) is manufactured. Bisimide is an intermediate product in the manufacture of many various resins, such as but not limited to ULTEM® resin (registered Trademark General Electric Co.). Therefore, the determination of stoichiometry is important in the manufacture of resins.

Typically, the manufacture of EPA disodium salt is a batch process with a molar ratio of ingredient at about a 1:2 ratio in an aqueous solution. An aqueous salt solution is then analyzed, by methods known in the art, to determine an amount of free EPA (protonated bisphenol A), which is related to the initial BPA:caustic ratio, or stoichiometry. Following the analyzing step, at least one corrective "add" of material is made to the contents of the reactor, and analysis is repeated, as needed.

The steps are repeated until an acceptable salt with a stoichiometry within a desired predetermined range is obtained. This repeating is, of course, time and labor intensive, all of which are ineffective and undesirable. Further, the repeated steps add possible error producing factors into the process. The error producing factors include, but are not limited to, adding improper amounts or inexact levels of materials, and allowing extra and foreign materials to exit and enter the reaction vessel. Furthermore, any existing error will be compounded by the additional errors. It has been observed that a large error amount causes process problems, which result in significant and undesirable losses.

The determination of a stoichiometry requires determining and measuring parameters for various characteristics of the material. Various methods for determining and measuring parameter values have been proposed. For example, it has been has proposed to use sound velocity probes, in conjunction with toroidal AC conductivity probes, to track a continuous acid-base equilibrium process, to determine stoichiometry parameter values.

As an example, in a batch process that scrubs chlorine gas with caustic (NaOH) to produce salts (NaCl), to determine the stoichiometry of the salts, caustic (NaOH) depletion and salt (NaCl) formation can be tracked by a single measurement, for example by a sound velocity. This single measurement is possible because in an ideal batch process a stoichiometry of caustic (NaOH) to salt (NaCl) is known. However, in this batch processes, the caustic (NaOH) must be continuously replenished. Thus, the stoichiometry of caustic (NaOH) to salt (NaCl) is not known because the measurement of added materials is not always exact, and there is an inherent loss of materials, both vapor and liquid, from the reaction vessel during the addition of materials. Thus, the exact stoichiometry of materials in the reaction vessel will not always be known.

Therefore, another independent measurement, such as a conductivity measurement, is needed to resolve and determine both the stoichiometry and the caustic (NaOH) concentration in the batch process. This additional independent measurement is, of course, time consuming, labor intensive, and a source of further errors.

The development of a "map" or predetermined relationship for conductivity, sound velocity, and temperature as a function of caustic (NaOH) concentration and caustic (NaOH)/salt (NaCl) stoichiometry has been suggested to form a general approximated stoichiometry solution, and reduce possible errors. A process was investigated in an attempt to derive such a predetermined relationship. The process provided a sample of hot, about 90° C., sodium hydroxide. Known amounts of an "add", bisphenol A, were added or "spiked" a number of times into the sample. Sound velocity, conductivity, and temperature of the sample were then independently measured, for example with commercially available stainless steel sound velocity probes or sensors. Normally, a conductivity probe produces an output signal, which is corrected for temperature. However, commercially available temperature probes used in the process include a protective polymer coating, under which the temperature probe is buried. Accordingly, a probe used for such measurements has a relatively slow response time, and the conductivity data must be logged in a raw uncorrected form.

The results of this process and its stoichiometry determination were, at best, inconclusive, since there was no independent measurement of stoichiometry error SE, other than a calculation based on measured constituents used in the process including those possible error producing added constituents. The obtained data could merely be fit to a "least squares" analysis to determine an arbitrary generalized approximation function for stoichiometry error SE from the data collected. This fit to a "least squares" analysis provided an arbitrary generalized approximation function for stoichiometry error SE is set forth in Equation (1):

$$SE = \sum_{i,j} K_{ij} a_i b \qquad (1)$$

In Equation (1), K is a constant and a and b are measured variables, such as for example, velocities, conductivities, and temperatures.

The arbitrary generalized approximation function for stoichiometry error SE in Equation (1) produced a rough calculated generalized approximated stoichiometry error SE from measured variables. However, the determined stoichiometry error SE is only within a range of about ±1.0% of a standard stoichiometry error SE. However, an error of about ±1.0% is not acceptable because of error producing factors.

Accordingly, an accurate and reliable stoichiometry process, and a similarly an accurate and reliable measurement and determination of variables to determine stoichiometry error SE are needed to produce salts. This method for the determination of stoichiometry error SE is especially useful in the ultimate practical and efficient manufacture of resins, without errors and process problems.

SUMMARY OF THE INVENTION

The invention is related to a method for a salt production and an accurate and reliable stoichiometry process, and a similarly an accurate and reliable measurement and determination of variables to determine stoichiometry error SE are needed to produce salts, that overcomes the above noted, and other, deficiencies.

In particular, the invention provides for determining a stoichiometry error SE of a sample comprises determining temperature of the sample; determining an on-stoichiometry conductivity of the sample; determining an on-stoichiometry sound velocity of the sample; and determining a nominal operating temperature point. The stoichiometry error SE for a sample is determined by:

$$SE = A \times (\sigma(1-c_\sigma(T-T_o)) \times (1-d(\upsilon(1+c_\upsilon(T-T_o))-\upsilon_{To}))-(\sigma_{To})$$

where:

SE=calculated stoichiometry error (mole-% excess BPA);

$\sigma$=measured conductivity (mS/cm);

$\upsilon$=measured sound velocity (m/s);

T=measured temperature (deg C);

$\upsilon_{To}$=sound velocity (m/s);

$\sigma_{To}$=mS/cm, conductivity at "normal" operating conditions;

A=a proportionality constant that scales conductivity into mole-% excess BPA(mole-%)/(mS/cm), $c_\sigma$=a linear temperature correction factor for conductivity (1/deg C);

$c_\upsilon$=a linear temperature correction factor for sound velocity(1/degC), d=a linear factor to adjust conductivity for sound velocity(s/m).

In accordance with the invention, a method for making bisphenol salt as the result of the reaction between bisphenol and an alkali metal hydroxide comprises preparing an aqueous bisphenol salt solution from substantially equivalent amounts of bisphenol and alkali metal hydroxide; contacting at least a portion of the aqueous solution bisphenol salt solution with an immiscible organic solvent to produce a two phase mixture; obtaining a value of the organic phase of the two phase mixture; determining alkali metal hydroxide variance from stoichiometry; adding at least one of additional alkali metal hydroxide and additional bisphenol to the aqueous bisphenoxide salt solution to obtain a bisphenoxide salt mixture having a substantial stoichiometry relation between alkali metal hydroxide and bisphenol; and separating water from the resulting aqueous bisphenoxide salt mixture to produce the anhydrous alkali metal bisphenoxide salt within about a ±0.2 mol % stoichiometry relationship between bisphenol and alkali metal hydroxide.

BRIEF DESCRIPTION OF THE DRAWINGS

While the novel features of this invention are set forth in the following description, the invention will now be described from the following detailed description of the invention taken in conjunction with the drawings, in which.

DETAILED DESCRIPTION OF THE EMBODIMENTS

Figure 1:
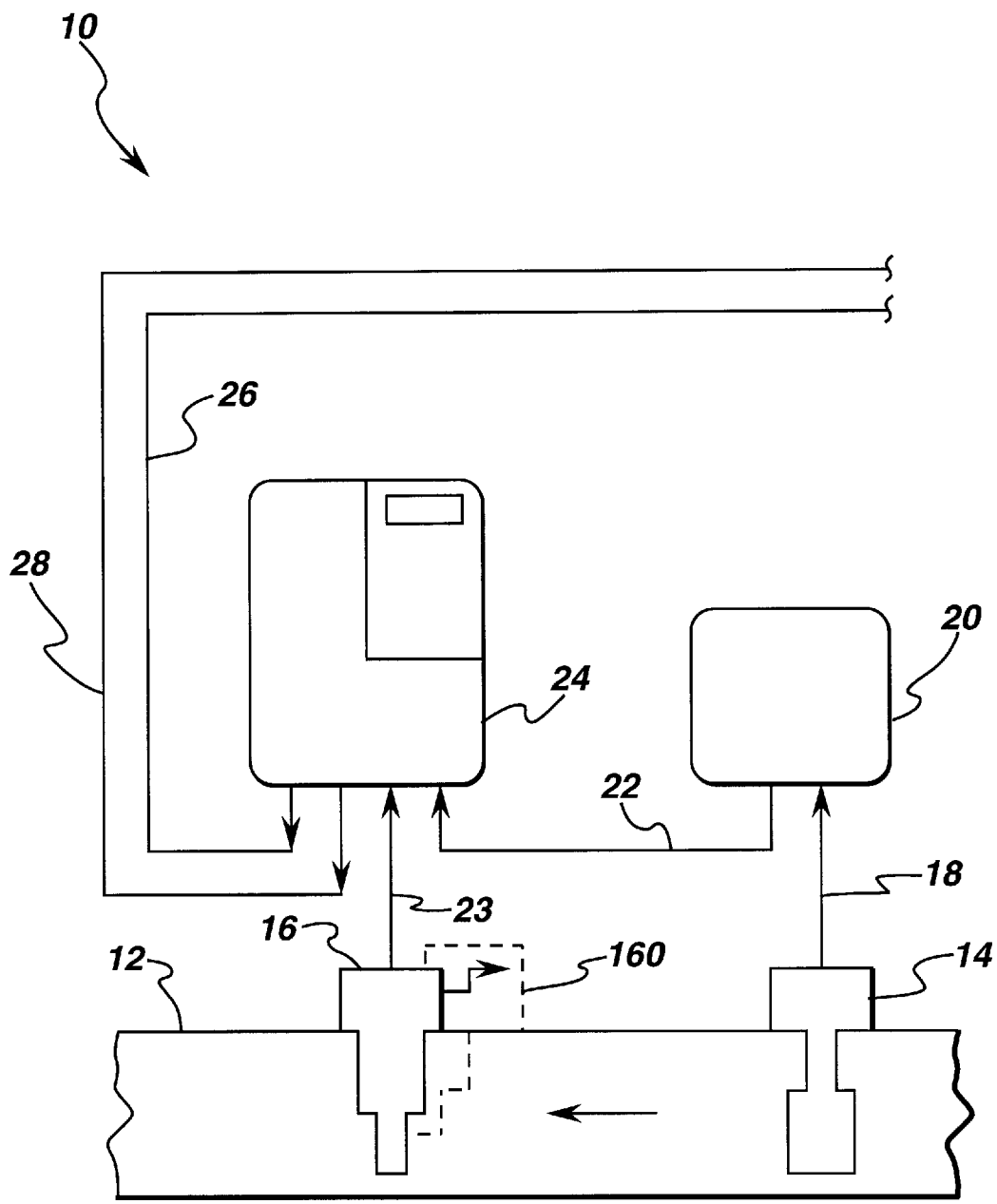
FIG. 1 is a schematic illustration of a sensor system, in accordance with the invention.

A method for making bisphenol salt as the result of the reaction between bisphenol, such as but not limited to bisphenol A, and an alkali metal hydroxide, such as but not limited to, sodium hydroxide and method to control the stoichiometry of bisphenol A and sodium hydroxide in the manufacture of BPA disodium salt has been described by Dellacoletta and Verbicky in U.S. Pat. No. 4,410,735, issued Oct. 18, 1983, assigned to the instant Assignee, the contents of which are fully incorporated by reference in this application. This method relies on a high pressure liquid chromatography (HPLC) analysis. The (HPLC) method to control the stoichiometry of bisphenol A and sodium hydroxide in the manufacture of BPA disodium salt is used in the manufacture of resins, such as ULTEM® resin, with considerable success.

A brief description of the Dellacoletta and Verbicky process will now be provided. A detailed description is found in the specification. For conventional BPA (bisphenol A, isopropylidenediphenol) disodium salt stoichiometry, a plant sample of BPA disodium salt in an aqueous salt solution is provided in a reactor. The plant sample is adjusted to about 10% solids with water, using a meter, such as a sound velocity meter, to measure percentage of solids. A sample of the aqueous solution, for example about 25 ml, is then extracted out, shaken with toluene for about 1 minute in a capped jar, container or reactor.

The phases are allowed to separate, for example for about 2 minutes, and a toluene phase is diluted with about 2 ml of acetonitrile. The sample is then analyzed by an appropriate method, such as but not limited to, a high pressure liquid chromatography (HPLC) to determine an amount of free BPA extracted into the toluene. The amount of extracted free BPA is related to an initial BPA:caustic ratio or stoichiometry in the plant sample of BPA disodium salt. While the Dellacoletta and Verbicky process provides for an efficient process and stoichiometry determination, it has been determined that there are several factors, that when controlled, can lead to an even more desirable process and stoichiometry determination.

It has been determined that an efficient and desirable controlled stoichiometry error is about ±0.2 mol % BPA, or about 11 pounds of BPA per batch process. This controlled stoichiometry error is about ±0.2 mol % BPA, or about 11 pounds of BPA per batch process results in a highly efficient salt and a desirably low stoichiometry error. The salt can be then used for the manufacture of other products, such as resins. Accordingly, controlling process parameters to obtain a stoichiometry error, about ±0.2 mol % BPA, is desirable.

It has also been determined that there are several key variables, that when controlled during a HPLC process, result in much tighter stoichiometry control. These include, but are not limited to, controlling an extraction temperature, controlling ambient atmosphere contact, controlling the solids percentage, and controlling an impurity level in BPA.

It has further been determined that the extraction temperature during a HPLC process, for an about 10% solids solution, provides a sample, that when analyzed, is important in the determination of an accurate, precise stoichiometry measurement. For example, using a lab prepared stoichiometry salt purified BPA and about 0.1N standard caustic, it was determined that about a ±1.0° C. difference in extraction temperature resulted in about a ±0.1 mol % BPA stoichiometry error of the aqueous salt, as determined during a HPLC process.

The background for this determination will now be discussed. Samples, when extracted from the plant, are hot. After these hot samples are diluted to about 10% solids, analysis occurs, either relatively quickly after dilution, or is delayed for several minutes. If a delay occurs during a HPLC process, the samples are cooled naturally, since laboratory ambient temperature during a HPLC process is not normally controlled. Since temperature is a characteristic that impacts other material characteristics, a poor extraction temperature control results in unsatisfactory parameter determination. This, of course, leads to a poor stoichiometry result.

Accordingly, it is desirable to control temperatures throughout the HPLC process to result in a desirable and accurate determination of stoichiometry. With controlled temperature during a HPLC process to within about ±1.0° C., salt standards, prepared with pure BPA and 1N NaOH, were within ±0.2 mol % BPA stoichiometry error. This ±0.2 mol % BPA stoichiometry error is highly desirable and efficient in the process of salts.

It was also observed that a sample, which had been adjusted to about 10% solids, absorbed varying amounts of carbon dioxide from the ambient atmosphere during a HPLC process. This absorption effectively neutralized the BPA disodium salt to a small, yet measurable extent. This neutralization during a HPLC process is undesirable since it results in a stoichiometry error for the salt. Accordingly, the contact to ambient atmosphere was directly related to a stoichiometry error of the sample, when determined by the HPLC process.

Therefore, it has been determined that exposure time of a sample to ambient atmosphere during a HPLC process was detrimental to the overall stoichiometry process. The exposure of a sample to ambient atmosphere must be controlled to avoid significant absorption of carbon dioxide into the sample. Preferably, the contact to carbon dioxide should be avoided, and, at least, a contact "hold" time to the ambient atmosphere should be minimized and controlled during a HPLC process for desirable results.

It was further determined that controlling a percent solids of a diluted plant sample during a HPLC process was important in determining stoichiometry error. If the adjusted percent solids for an original sample during a HPLC process were not controlled and held within a predetermined range of a set solids percentage level, a reliable stoichiometry error could not be determined.

For example, it was determined that if adjusted percent solids for an original sample during a HPLC process were within about ±0.4% of about 10.0% solids, a reliable stoichiometry error could be determined. Accordingly, controlling a percent solids of a diluted plant sample during a HPLC process to within about ±0.4% of about 10.0% solids is important in determining stoichiometry error.

It was also observed that BPA from different sources do not possess desirable characteristics for use with a stoichiometry test, even when an extraction temperature, hold time, and percent solids of the diluted plant sample are closely controlled during a HPLC process.

These undesirable results were determined to be a result of organic impurities in certain sources of BPA. Further, it was determined that these organic impurities coelute with internal standards in the HPLC process analysis of the final stoichiometry sample. The amount of free BPA extracted into internal standards during a HPLC process is related to an initial stoichiometry of the sample, and the amount of free BPA in the toluene extract is determined using toluene as an internal standard. Accordingly, this large degree of error associated with the coelutation leads to a large stoichiometry error.

Once this error associated with the coelutation was discovered, the stoichiometry error is compensated for during a HPLC process, by making stoichiometry standards in accordance with the source of BPA, and modifying the HPLC analytical process accordingly in light of the source of BPA.

The above compensation of stoichiometry control in light of the above factors, during a HPLC process for preparing BPA salt, reduces stoichiometry error from about ±1.5 mol % to about ±0.2 mol % stoichiometry error. This marked improvement is extremely desirable since it resulted in increased cycle time in the overall process. The improvement also resulted in less process down time for cleaning of off-stoichiometry salt from salt dryers and associated equipment.

The description herein refers to disodium salt, however the invention includes other alkali metals in the salt. These alkali metals include for example, sodium, potassium, and lithium. Further, the description of the invention includes other bisphenols, in addition to BPA. For example, the bisphenols, which can be converted to alkali metal salts, in accordance with the invention comprise, for example, 2,2-bis(2-hydroxyphenyl)propane; 2,4'-dihydroxydiphenylmethane; bis(2-hydroxyphenyl)methane; 2,2-bis(4-hydroxyphenyl)propane, hereinafter identified as "bisphenol-A" or "BPA";(4-hydroxyphenyl)-2(3'-hydroxyphenyl)propane; 1,1-bis(4-hydroxyphenyl)ethane; 1,1-bis(4-hydroxyphenyl)propane; 2,2-bis(4-hydroxyphenyl)pentane; 3,3-bis(4-hydroxyphenyl)pentane; 4,4'-dihydroxybiphenyl; 4,4'-dihydroxy-3,3',5,5'-tetramethylbiphenyl; 2,4'-dihydroxybenzophenone; 4,4'-dihydroxydiphenyl sulfone; 2,4'-dihydroxydiphenyl sulfone; 4,4'-dihydroxydiphenyl sulfoxide; 4,4'-dihydroxydiphenyl sulfide; hydroquinone; resorcinol; 3,4'-dihydroxydiphenylmethane; 4,4'-dihyroxybenzophenone; and 4,4'-dihydroxydiphenyl ether.

A sensor system and method to control salt stoichiometry uses a modified HPLC process, as discussed above. The sensor system and method to control salt stoichiometry determines salt stoichiometry and salt stoichiometry error SE as set forth below.

A first preferred embodiment of the sensor system to control salt stoichiometry invention is illustrated in FIG. 1, which shows hardware used in the sensor system, in accordance with the invention. The hardware comprises known features, and similar features could be used for disclosed features.

A dual sensor input system 10, as illustrated in FIG. 1, comprises a reactor or container 12, such as a conduit, into which at least two sensors are placed. A conductivity sensor 14 is placed at an upstream location in the reactor 12. The conductivity sensor 14 may be any known conductivity sensor, for example a toroidal conductivity sensor.

A sound velocity sensor 16 is located downstream from the conductivity sensor 14 in the reactor 12. The sound velocity sensor 16 may be coupled with a temperature sensor 160 (illustrated in phantom). Alternatively, the temperature sensor may be formed integral with the sound velocity sensor 16. The sensors 14 and 16, and 160 if separately provided are used in the determination of variables, which are used to determine a stoichiometry.

The dual sensor system 10 further comprises an input lead 18, which connects the conductivity sensor 14 to a conductivity transmitter 20. An output lead 22 extends from the conductivity transmitter to a processor 24, for example a sonic analyzer. An output lead 23 from the sound velocity sensor 16 also extends to the processor 24. The processor 24 can be any appropriate electronic device that can process signals by the HPLC process discussed above, in accordance with the invention.

At least two outputs 26 and 28 extend from the processor 24 and are connected to a display or similar monitor (not illustrated). The monitor permits an operator access to the data obtained from the sensors. A first output 26 of the at least two outputs may be a temperature output, and a second output 28 of the at least two outputs may be a concentration output. Of course, more than two outputs may be provided. Further, the outputs may be grouped together as a single output wire that is capable carry a plurality of signals.

The stoichiometry determination process, in accordance with the invention, involves simultaneous acquisition of parameters of the sample in the reactor 12. These parameters include, but are not limited to, sound velocity, conductivity, and temperature data. These parameters are for use in the HPLC process, described above.

Further, the process controls the determination of variables, for the process as discussed above, and involves processing of acquired data to determine, i.e., calculate, a stoichiometry error SE. The stoichiometry error SE, in accordance with the invention, uses a linear temperature correction for sound velocity and linear temperature, and sound velocity corrections for conductivity.

The process utilizing the sensor system 10 to obtain data will now be described. The process that is being monitored is a batch process. The process controls ambient temperature, ambient atmosphere contact, percent solids, by using differrnt sources of BPA standards and biasing HPLC analysis process described above to account for organic impurities, to obtain a controlled HPLC process and result. Therefore, the process results in less "adds" so an overall possibility of an error is significantly reduced.

The process uses the sensor system 10 to obtain controlled data. The probes 14 and 16 are placed in the reactor 12 and immersed in samples at about 90° C. Sound velocity, temperature, and conductivity data parameters are then measured, in accordance with the control HPLC method, as discussed above. The measured data parameters, determined using the controlled HPLC analytical method described above, are then investigated to determine a possible relationship with respect to a standard independently determined stoichiometry error SE.

A mathematical formula was determined to relate determined stoichiometry error SE, for example of disodium salt, to measured parameter values of conductivity $\sigma$, sound velocity $\upsilon$, and temperature T. The stoichiometry error SE was determined as in Equation (2):

$$SE = A \times (\sigma(1-c_\sigma(T-T_0)) \times (1-d(\upsilon(1+c_\upsilon(T-T_o))-\upsilon_{T0})) - \sigma_{T0}) \quad (2)$$

where:

SE=calculated stoichiometry error (mole-% excess BPA);
$\sigma$=measured conductivity (mS/cm);
$\upsilon$=measured sound velocity (m/s);
T=measured temperature (deg C);
$\upsilon_{To}$=sound velocity (m/s);
$\sigma_{To}$=mS/cm, conductivity at "normal" operating conditions;
A=a proportionality constant that scales conductivity into mole-% excess BPA(mole-%)/(mS/cm),
$c_\sigma$=a linear temperature correction factor for conductivity (1/deg C);
$c_\upsilon$=a linear temperature correction factor for sound velocity(1/degC),
d=a linear factor to adjust conductivity for sound velocity(s/m).

In Equation (2), it is assumed that the measured conductivity can be corrected for sound velocity and temperature. This correction yields a quantity, which exhibits a linear relationship with stoichiometry error SE. Thus, assuming that a linear relationship holds for a small range around "zero" stoichiometry error, Equation (2) is dependent on obtaining a plant stoichiometry within a few percent of about zero. This obtaining a plant stoichiometry within a few percent of about zero is achieved, for example, by accurately weighing out initial ingredients.

A standard independently determined stoichiometry error se is determined, for example, as an independent test stoichiometry error se from a standard laboratory method using ultra pure materials and controlled conditions, as is known in the art. These ultra pure materials and controlled conditions are not suitable for use in a plant environment.

Figure 2:
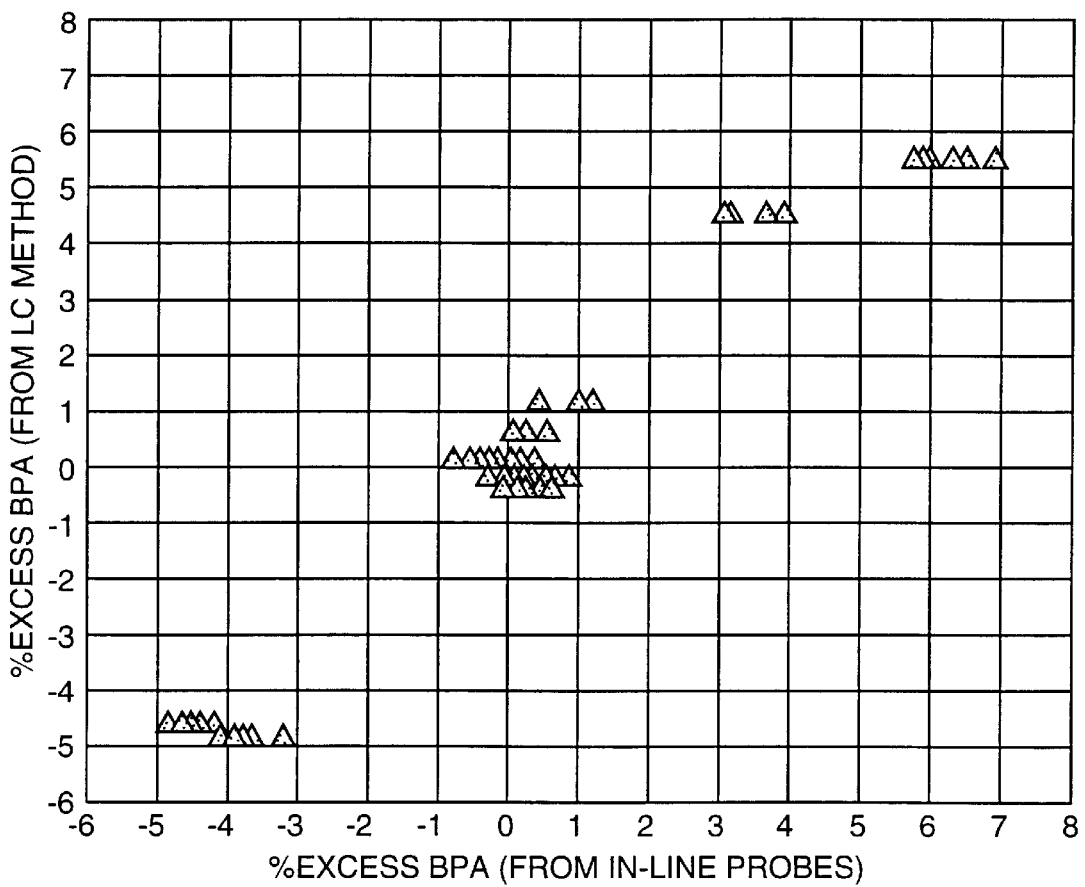
FIG. 2 is a graphic representation of determined stoichiometry error, in accordance with the invention.

In determining a relationship between an independent test stoichiometry error se and the determined stoichiometry error SE, which was determined as a result to the measured parameters, the measured data was plotted, as in FIG. 2. In FIG. 2, the measured stoichiometry error from the controlled HPLC method is plotted on the Y-axis, and the predicted stoichiometry error as in Equation (2) is plotted along the X-axis.

In the above described process, the dual sensor system 10 determines process parameters. The data obtained by probes 14 and 16 is logged by a processor 24 on a data acquisition system. Data logged by the data acquisition system is used to measure temperature coefficients, $c_\upsilon, c_\sigma$. Thus, in accordance with the invention, the temperature coefficients, $c_\upsilon c_\sigma$ are predetermined and constant for all stoichiometry determinations.

Therefore, the constant nature of the temperature coefficients, $c_\upsilon, c_\sigma$ reduces the number of variable parameters in Equation (2) from six to four. This, of course, is efficient and desirable since the reduction variables lessens any error associated with the determination as set forth in Equation (2).

Figure 3:
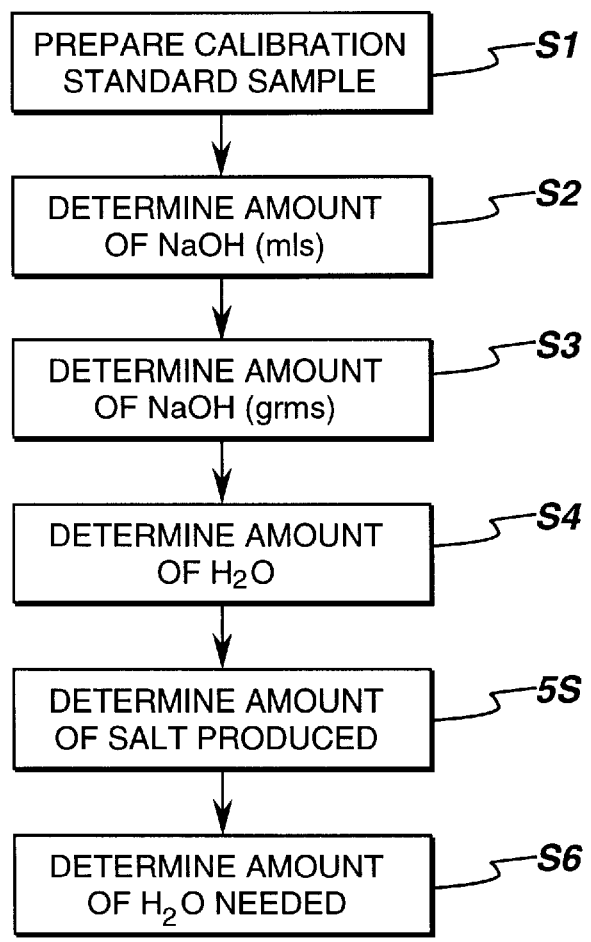
FIG. 3 is a flow chart for a process to determine stoichiometry error, in accordance with the invention.

An independent (test) stoichiometry error SE, for example to be used in the above determination, is determined in the following manner. To facilitate understanding of the determination, the Equations used in the determination are provided, and then parameters are applied to the Equations. Further, FIG. 3 is a flow chart of the application of the Equations to result in an independent (test) stoichiometry error se.

Initially, in step S1, a calibration standard sample is prepared according to the following chemical reaction:

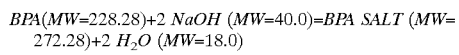

BPA(MW=228.28)+2 NaOH (MW=40.0)=BPA SALT (MW=272.28)+2 $H_2O$ (MW=18.0)

In the above chemical reaction, examples of the approximate moles and amounts, in grams, to equal the molecular weight times the desired moles are as set forth in Table I.

TABLE I

| BPA 0.025 moles = 5.707 grams |
|---|
| NaOH 0.05 moles = 2.0 grams |
| $H_2O$ 68.07 grams (to get to about 10% solids) |

This reaction produces about 0.025 moles or about 6.807 grams of BPA salt, using only recrystallized BPA, about 1N NaOH with DI $H_2O$. 1N NaOH is one molecular weight, in grams, of NaOH about 40.0 per liter of $H_2O$. Therefore, about 1.0 grams of NaOH per about 25 mls of $H_2O$ result, where the density of 1N NaOH is approximately 1.040.

Theoretical approximated amounts of BPA, NaOH and DI $H_2O$, if using about 1.00N NaOH, is set forth in Table II, as follows:

TABLE II

| BPA | 5.707 grams |
|---|---|
| 1N NaOH | 50 mls |
| DI $H_2O$ | 19.2 mls |

Accordingly, a chemical reaction as above, will produce a near perfect stoichiometry BPA salt at about 10% solids. This would present an ideal near perfect stoichiometry BPA salt at about 10% solids for use in determining stoichiometry error.

However, since 1.00N NaOH is not usually commercially available, the actual normality of the NaOH must be included in a calculation to obtain the about 2.0 grams of NaOH, which is needed for a calibration standard. The 1N NaOH used will be weighed to include density, at about 1.040, in the calculation. The following calculations to obtain about 2.0 grams of NaOH needed for a calibration standard are based on a 0.984N NaOH solution, which is the closest commercially available NaOH solution available.

To determine an amount of 0.984N NaOH solution required to produce about 2.0 grams of NaOH, the following determinations were conducted, in accordance with Equations (3) and (4), in steps S2 and S3.

1000 mls/MW of NaOH/actual normality * (amount of NaOH needed)=mls of 0.984N NaOH needed. (3)

Using parameters in Equation (3):

1000/40/0.984 * 2.0=50.813 mls (mls of 0.984N NaOH needed* density of 1N NaOH)=grams of NaOH needed to produce about 2.0 grams of NaOH (4)

Using parameters in Equation (4):
(50.813 * 1.040)=52.846 grams of 01984N NaOH needed to produce about 2.0 grams of NaOH Therefore, to determine how much DI $H_2O$ is needed to produce about a 10% solids solution, it is necessary to determine how much $H_2O$ is in the 0.984N NaOH solution. The amount of $H_2O$ produced by the reaction and the amount of BPA salt produced by the reaction are determined by the equations (5) and (6), respectively, in steps S4 and S5:

(Actual grams of 0.984N NaOH solution)−(amount of NaOH needed)=amount of $H_2O$ in the 0.984N NaOH solution (5)

Using parameters in Equation (5):

| 52.846 | (grams of 0.984N NaOH solution) |
| −2.000 | (grams of NaOH needed) |
| 50.846 | (grams of $H_2O$ in 52.846 grams of 0.984N NaOH solution) |

(Moles of $H_2O$ produced) * (MW of $H_2O$) * (moles of product produced)=grams of $H_2O$ produced by the reaction (6)

Using parameters in Equation (6):

| | 2.0 | (moles of $H_2O$ produced by reaction) |
| × | 18.0 | (MW of $H_2O$) |
| | 36.0 | |
| × | 0.025 | (moles of product produced) |
| | 0.90 | (grams of $H_2O$ produced by reaction) |

To obtain about 10% solids, the grams of product produced is multiplied 10 times, the amount of $H_2O$ in the 0.884N NaOH solution (Equation (5)) is subtracted and the grams of $H_2O$ produced by the chemical reaction (Equation (6)) are subtracted, in step S6.

| | 6.807 | (grams of product) |
| × | 10.0 | |
| | 68.07 | (total grams of product and $H_2O$ needed) |
| − | 50.85 | (grams of $H_2O$ in 52.846 grams of 0.984N NaOH) |
| | 17.22 | |
| − | 0.90 | (grams of $H_2O$ produced) |
| | 16.32 | (grams of $H_2O$ needed) |

Figure 4:
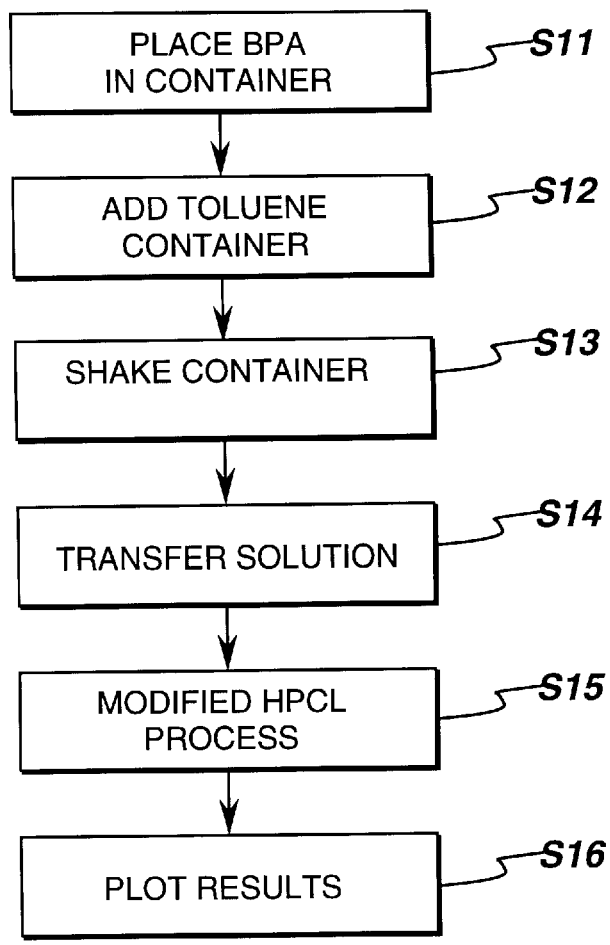
FIG. 4 is a flow chart of a process to determinate a calibration standard, in accordance with the invention.

The process to determine a calibration standard sample as applied in step S1, will now be discussed in detail with reference to FIG. 4. In step S11, about 10 milligrams of recrystallized BPA were placed in a container. In step S12, about 100 mls of toluene were added to the container. Next, the container and contents were shaken until the BPA is dissolved in step S13.

In step S14, some of this solution, for example about 2 mls, is transferred into a high pressure liquid chromatography (HPLC) vial. The modified HPLC process is then used, in step S15, to determine a stoichiometry. Next, the resultant stoichiometry error SE is plotted in step S16, with the stoichiometry error as determined from measured parameters.

The instant invention can also be applied to determine stoichiometry error parameters for use in determining a stoichiometry error. This determination of parametners comprises analyzing at least two, and preferably more than two samples liquid, to determine a stoichiometry error and applying the determined stoichiometry error to determine a proportionality constant for determining stoichiometry error parameters for use in Equation (2).

Figure 5:
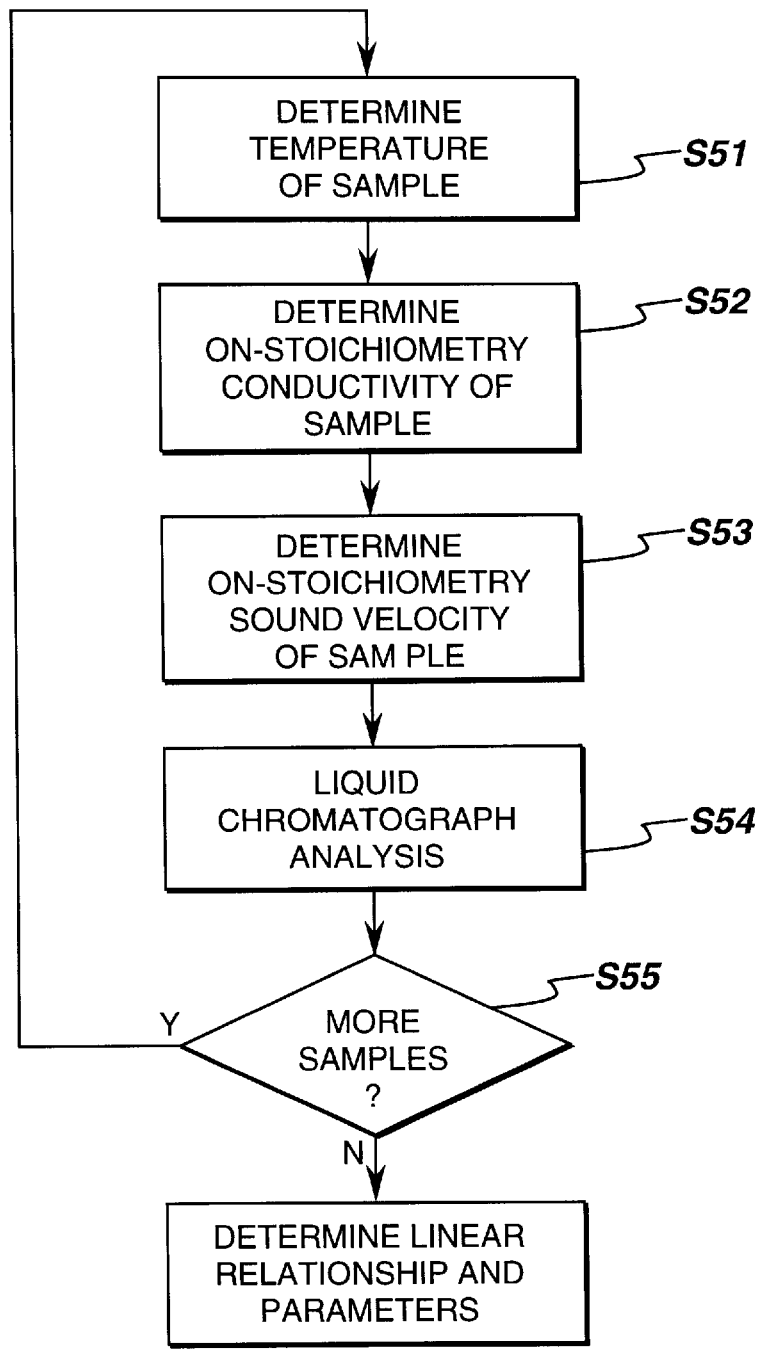
FIG. 5 is a flow chart for determining a proportionality constant for determining stoichiometry error parameters, in accordance with the invention.

An explanation of the method to determine stoichiometry error parameters will now be discussed in detail, with reference to the flow chart of FIG. 5. Initially, at step S51, the temperature of a sample is determined. Next at step S52, an on-stoichiometry conductivity of the sample at a nominal operating temperature is determined. At step S53, an on-stoichiometry sound velocity of the sample at a nominal operating temperature is determined.

At step S54, a stoichiometry error by a liquid chromatographic analyzation is determined, in accordance with the invention. Steps S51–S54 are repeated for each sample available. The determination of a proportionality constant for determining stoichiometry error parameters requires only two different samples to be measured and analyzed. However, it has been determined even more preferable results are obtained if the number of samples measured and analyzed is greater than two.

The process then determines if there are any more samples to be analyzed, at step S55. If there are more samples to be analyzed, the process repeats steps S51–S54, as necessary. When there are no remaining samples to be measured and analyzed, the process moves to step S56, to determine a linear relation between stoichiometry error and temperature, conductivity and sound velocity according to Equation (2):

$$SE = A \times (\sigma(1-c_\sigma(T-T_0)) \times (1-d(\upsilon(1+c_{T0}(T-T_a))-\upsilon_{T0}))-\sigma_{T0}) \quad (2)$$

by a least squares analysis. The least squares analysis relies upon the determined values in steps S51–55 to provide stoichiometry paramenters. These parameters include at least one of: $\sigma$, which is a measured conductivity (mS/cm); $\upsilon$ which is a measured sound velocity (m/s); T which is a measured temperature (deg C); $\upsilon_{T0}$ which is a sound velocity (m/s); $\upsilon_{T0}$ which is conductivity at "normal" operating conditions (mS/cm); A which is a proportionality constant that scales conductivity into mole-% excess BPA (mole-%)/(mS/cm); $c_o$ which is a linear temperature correction factor for conductivity (mole-%)/(mS/cm)(1/deg C); $c_\upsilon$ which is a linear temperature correction factor for sound velocity(1/degC);d which is a linear factor to adjust conductivity for sound velocity(s/m).

Alternatively, the process is conducted by measuring all paramenters A, $c_\upsilon$, $c_o$, $\sigma_{T_0}$, $\upsilon_{T_0}$, and d and determining a linear relation, as above. Further, one or more of the parameters may be measured and the remainder of the parameters can be determined as above.

The determining a stoichiometry error by a liquid chromatography analysis in step S54 comprises making bisphenol salt as the result of the reaction between bisphenol and an alkali metal hydroxide. The method further comprises preparing an aqueous bisphenol salt solution from substantially equivalent amounts of bisphenol and alkali metal hydroxide; contacting at least a portion of the aqueous solution bisphenol salt solution with an immiscible organic solvent to produce a two phase mixture; obtaining a value of the organic phase of the two phase mixture; determining alkali metal hydroxide variance from stoichiometry; adding at least one of additional alkali metal hydroxide and additional bisphenol to the aqueous bisphenoxide salt solution to obtain a bisphenoxide salt mixture having a substantial stoichiometry relation between alkali metal hydroxide and bisphenol; and separating water from the resulting aqueous bisphenoxide salt mixture to produce the anhydrous alkali metal bisphenoxide salt within about a ±0.2 mol % stoichiometry relationship between bisphenol and alkali metal hydroxide.

While the embodiments described herein are preferred, it will be appreciated from the specification that various combinations of elements, variations or improvements therein may be made by those skilled in the are that are within the scope of the invention.

What is claimed is:

1. A method for making bisphenol salt as the result of the reaction between bisphenol and an alkali metal hydroxide, the method comprising:

preparing an aqueous bisphenol salt solution from stoichiometric amounts of bisphenol (1 part) and alkali metal hydroxide (2 parts);

contacting at least a portion of the aqueous solution bisphenol salt solution with an immiscible organic solvent to produce a two phase mixture;

obtaining a value representative of an amount of the organic phase of the two phase mixture;

determining alkali metal hydroxide variance from actual stoichiometry, the determining comprising:

removing a sample of an aqueous solution of BPA salt from a process vessel;

adjusting the aqueous solution of BPA salt to obtain a constant solids value at about 10% solids using a sound velocity meter in a controlled environment;

providing an equal volume of toluene to the aqueous solution of BPA salt;

mixing the about 10% solution and the toluene at 25° C.±1.0° C.;

extracting free BPA from the aqueous phase into the toluene;

allowing the phases to separate, with the toluene as an organic phase and an aqueous BPA salt phase, at about 25° C.±1.0° C.:

analyzing toluene phase and determining the amount of free BPA in the toluene by HPLC;

relating the amount of BPA in the toluene phase to the actual stoichiometry of the aqueous solution of BPA;

adding at least one of additional alkali metal hydroxide and additional bisphenol to the aqueous bisphenoxide salt solution to obtain a bisphenoxide salt mixture having a substantial stoichiometry relation between alkali metal hydroxide and bisphenol; and separating water from the resulting aqueous bisphenoxide salt mixture to produce the anhydrous alkali metal bisphenoxide salt within about a ±0.2 mol % stoichiometry relationship between bisphenol and alkali metal hydroxide.

2. A method according to claim 1, where the bisphenol is bisphenol-A.

3. A method according to claim 1, where the immiscible organic solvent is toluene.

4. A method according to claim 1, where the alkali metal hydroxide is sodium hydroxide.

5. A method according to claim 1, further -comprising controlling a percentage solids to about ±0.4% of about 10.0% solids.

6. A method according to claim 1, further comprising controlling contact with ambient atmosphere.

7. A method according to claim 6, further comprising controlling contact with ambient atmosphere to avoid absorption of carbon dioxide into the sample.

8. A method for determining stoichiometry error SE of a sample, the method comprising:

determining temperature of the sample;

determining conductivity of the sample; and determining sound velocity for the sample;

where stoichiometry error SE for a sample is determined by:

$$SE = A \times (\sigma(1-c_\sigma(T-T_0)) \times (1-d(\upsilon(1+c_y(T-T_o))-\upsilon_{T0}))-\sigma_{T0})$$

where SE equals calculated stoichiometry error (mole-% excess BPA); σ equals measured conductivity (mS/cm): υ equals measured sound velocity (m/s); T equals measured temperature (deg C); $\upsilon_{T0}$ equals sound velocity (m/s): $\sigma_{TO}$ equals conductivity at "normal" operating conditions (mS/cm); A is a proportionality constant that scales conductivity into mole-% excess BPA (mole-%) / (mS/cm): $c_o$ equals a linear temperature correction factor for conductivity (1/deg C),: $c_y$ equals a linear temperature correction factor for sound velocity (1/degC): d equals a linear factor to adjust conductivity for sound velocity (s/m).

9. A method according to claim 8, where the determining temperature of the sample; the determining the conductivity of the sample; and the determining the sound velocity of the sample comprise:

sensing temperature, sound velocity and conductivity with at least one sensor.

10. A method according to claim 9, where the sensing temperature and conductivity with at least one sensor comprises sensing temperature and sound velocity with a first sensor assembly and sensing conductivity with a second sensor assembly.

11. A method according to claim 9, where the first sensor assembly comprises a sound velocity and temperature sensor.

12. A method according to claim 11, where the first sensor assembly comprises a sound velocity sensor and a separate temperature sensor.

13. A method according to claim 12, where the temperature sensor is coupled with the sound velocity sensor.

14. A method according to claim 8, where the temperature coefficients, $c_v, c_o$, the on-stoichiometry conductivity $\sigma_{T_0}$; and the on-stoichiometry sound velocity $v_{T_0}$ are predetermined and constant.

15. A method for determining stoichiometry error parameters between samples, the method comprising:

(1) determining temperature of a first sample;

(2) determining on-stoichiometry conductivity of the sample at a nominal operating temperature;

(3) determining on-stoichiometry sound velocity at a nominal operating temperature;

(4) determining a stoichiometry error by a liquid chromatographic analyzation;

(5) repeating steps (1)–(5) for at least second sample;

(6) determining a linear relation between stoichiometry error and temperature, conductivity and sound velocity according to:

$$SE = A \times (\sigma(1-c_o(T-T_0)) \times (1-d(v(1+c_y(T-T_o))-v_{T0}))-\sigma_{T0})$$

by a least squares analysis to determine at least one parameter selected from the group of:

$\sigma$ that is a measured conductivity (mS/cm); $v$ that is a measured sound velocity (m/s); T that is a measured temperature (deg C): $v_{T_0}$ that is a sound velocity (m/s): $\sigma_{T0}$ that is a conductivity at "normal" operating conditions (mS/cm): A that is a proportionality constant that scales conductivity into mole-% excess BPA (mole-%) / (mS/cm); $c_o$ that is a linear temperature correction factor for conductivity (1/deg C),: $c_y$ that is a linear temperature correction factor for sound velocity (1/degC): d that is a linear factor to adjust conductivity for sound velocity (s/m).

16. A method according to claim 15, where the determining a stoichiometry error comprises:

preparing a solution from substantially equivalent amounts of constituents;

contacting at least a portion of the solution with an organic solvent to produce a two phase mixture;

obtaining a value representative of an amount of the organic phase of the two phase mixture;

determining variance from stoichiometry;

adding at least one of constituent to the solution to obtain a mixture having a substantial stoichiometry relation between the constituents; and separating water from the resulting mixture to produce about a 0.2 mol % stoichiometry relationship between the constituents.

17. A method according to claim 15, further comprising measuring one or more of the parameters and determining the remainder of the parameters by a least squares analysis.

* * * * *